United States Patent
Morman et al.

(10) Patent No.: US 6,579,274 B1
(45) Date of Patent: Jun. 17, 2003

(54) BREATHABLE LAMINATE PERMANENTLY CONFORMABLE TO THE CONTOURS OF A WEARER

(75) Inventors: Michael Tod Morman, Alpharetta, GA (US); Patricia Hsiaoyin Hwang, Alpharetta, GA (US); Audrie Tomoko Ono, Atlanta, GA (US); Howard Martin Welch, Woodstock, GA (US); Charles John Morell, Roswell, GA (US); Sjon-Paul Lee Conyer, Roswell, GA (US); Duane Girard Uitenbroek, Little Chute, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 23 days.

(21) Appl. No.: 09/651,914

(22) Filed: Aug. 31, 2000

Related U.S. Application Data

(63) Continuation-in-part of application No. 09/460,490, filed on Dec. 14, 1999.

(51) Int. Cl.$^7$ ................................................ A61F 13/15
(52) U.S. Cl. ............................. 604/385.22; 604/385.16
(58) Field of Search ...................... 604/385.16, 385.22; 442/394, 398

(56) References Cited

U.S. PATENT DOCUMENTS

| | | | |
|---|---|---|---|
| 3,338,992 A | 8/1967 | Kinney | 264/24 |
| 3,341,394 A | 9/1967 | Kinney | 161/72 |
| 3,502,538 A | 3/1970 | Petersen | 161/150 |
| 3,502,763 A | 3/1970 | Hartmann | 264/210 |
| 3,542,615 A | 11/1970 | Dobo et al. | 156/181 |
| 3,692,618 A | 9/1972 | Dorschner et al. | 161/72 |
| 3,802,817 A | 4/1974 | Matsuki et al. | 425/66 |
| 3,849,241 A | 11/1974 | Butin et al. | 161/169 |
| 4,340,563 A | 7/1982 | Appel et al. | 264/518 |
| 4,965,122 A | 10/1990 | Morman | 428/225 |
| 5,322,728 A | 6/1994 | Davey et al. | 428/296 |
| 5,543,206 A | 8/1996 | Austin et al. | |
| 5,571,619 A | 11/1996 | McAlpin et al. | 428/364 |
| 5,582,903 A | 12/1996 | Levy et al. | |
| 5,770,529 A | * 6/1998 | Dennis et al. | 442/268 |
| 5,883,028 A | * 3/1999 | Morman et al. | 442/394 |
| 5,925,026 A | 7/1999 | Arteman et al. | 604/383 |
| 5,968,029 A | 10/1999 | Chappell et al. | 604/385.1 |
| 6,309,736 B1 | * 10/2001 | McCormack et al. | 428/198 |

FOREIGN PATENT DOCUMENTS

EP 604 731 7/1994

* cited by examiner

Primary Examiner—Dennis Ruhl
Assistant Examiner—Michael G. Bogart
(74) Attorney, Agent, or Firm—Pauley Petersen Kinne & Erickson

(57) ABSTRACT

A breathable, substantially liquid impermeable laminate is provided that is permanently conformable to the contours of a wearer's body when used in a personal care absorbent article or a medical article. The laminate includes a breathable (preferably microporous) film and a fibrous nonwoven web. Both the film and the web are extendible in a cross direction to a width at least 25% greater than an original, unstretched width upon application of a stretching force. The web and the film, and the overall laminate, exhibit little or no retractive force once they have been stretched. A diaper or other garment can be constructed in undersized fashion using the laminate, permitting material savings. When the garment is worn, the laminate stretches only where needed to provide a substantially perfect fit on the wearer. The minimal retractive force avoids the skin marks, rashes, etc. that can result from elastic garments.

69 Claims, 3 Drawing Sheets

BREATHABLE LAMINATE PERMANENTLY CONFORMABLE TO THE CONTOURS OF A WEARER

This application is a Continuation-In-Part of application Ser. No. 09/460,490 filed Dec. 14, 1999.

FIELD OF THE INVENTION

This invention relates to a breathable laminate (i.e., breathable to water vapor but substantially liquid-impermeable) which is permanently conformable to the contour of a wearer. The laminate stretches as needed to conform to the contour of the wearer and remains, essentially, in its extended or stretched state, even after a stretching force is removed.

BACKGROUND OF THE INVENTION

Laminates which are breathable to water vapor but substantially impermeable to liquid water are known in the art, and are commonly used in diaper backings, other personal care absorbent garments, medical garments and the like. These laminates may be composed of a breathable, stretch-thinned filled film and a spunbond web. The breathable film can be formed by blending one or more polyolefins with an inorganic particulate filler, forming a film from the mixture, and stretching the film to cause void formation around the filler particles. The resulting film may have thin polymer membranes around the filler particles which permit molecular diffusion of water vapor, while the overall film substantially blocks transmission of liquid water, or may have micropores going through the film. The breathable film can be laminated to a nonwoven web, for instance, a spunbond web, by thermal or adhesive bonding. The spunbond web adds strength and integrity to the breathable laminate, and provides a soft, cloth-like feel.

One trend affecting the personal care absorbent garment industry, and the medical garment industry, involves the demand and need for products with higher breathability to water vapor, which retain or increase the barrier to water, blood and other liquid substances. This trend reflects the demand for increased wearer comfort without loss of barrier performance. Another trend affecting these industries involves the demand and need for products having better fit, which conform to the contours of the wearer's body. To date, much of the investigation in this area has involved use of elastic materials.

One challenge involving the use of elastic materials is that many of the products, including absorbent garments, have a complex layer structure. Absorbent garments typically include at least a liquid-permeable top layer, an absorbent core layer, and a breathable, substantially liquid-impermeable outer cover laminate. If one of these materials is made elastic, the absorbent garment will not necessarily be elastic. In order for the absorbent garment to have elastic properties, each layer must either a) exhibit a desired minimum level of stretching and retraction or b) be "free floating" and not attached to the elastic or extendible layers.

Another challenge of using elastic materials to promote conformability is the conversion of kinetic energy to potential energy during stretching. The stored potential energy in the stretched regions of the garment creates a retractive force which acts against the wearer's body, causing compression of the skin and discomfort. Wherever an elastic garment is stretched in selected regions to conform to a wearer's body, the garment will exhibit a tighter fit in the stretched regions. Skin ripples, red marks or even rashes may form where the elastic material exhibits the greatest retractive force against the wearer's skin. These problems become more acute when the garment contains more than one elastic layer.

There is a need or desire in the industries of personal care absorbent garments and medical garments, for less expensive materials which stretch in order to conform to the contours of a wearer's body. There is also a need or desire for materials which do not store significant amounts of potential energy when stretched, and which do not exhibit excessive retractive force against the wearer's body. In short, there is a need or desire for materials and garments which remain stretched, i.e., which permanently conform to the contours of the wearer's body.

SUMMARY OF THE INVENTION

The present invention is directed to a substantially liquid-impermeable laminate including at least one thermoplastic nonwoven filament web and at least one film, preferably a breathable, substantially liquid-impermeable film laminated to it. The laminate (which is preferably breathable) has a machine direction (direction of formation) which corresponds to a primary direction of orientation of the nonwoven filaments, and a cross direction which is perpendicular to the machine direction. The breathable laminate is extendible in the cross direction to a stretched width that is at least 25% greater than an original, unstretched width upon application of a stretching force. When the stretching force is removed, the breathable laminate either does not retract, or retracts by not more than 30% of the difference between the stretched width and the original width.

The breathable, substantially liquid impermeable laminate preferably includes a breathable, microporous film having cross-directional extendibility at least as great as the laminate, and a fibrous nonwoven web, bonded to the film, which also has cross-directional extendibility at least as great as the laminate. The film may alternatively be made of an inherently breathable polymer. The component which has the least cross-directional extendibility (whether the film or the web) will limit the useful cross-directional extendibility of the entire laminate. In other words, the laminate will extend to the same or a lesser extent than the least extendible layer. Similarly, neither the film nor the web should exhibit significantly more retractive force than is desired for the laminate in general. If either the film or the web has a tendency to retract by more than 30% of the difference between its stretched width and original unstretched width, then the overall laminate may retract too much or apply excessive retractive force against the wearer's body.

In one embodiment, the thermoplastic nonwoven filament web is a neck-stretched nonwoven web, for example, a neck-stretched spunbond web. The nonwoven web, which is made of a relatively inelastic polymer material, is extended in the machine direction to cause narrowing or neck-in of the web in the cross direction. The web is laminated and bonded to a breathable microporous film while the web is in the necked condition. The film includes at least one thermoplastic polymer which renders the film stretchable (but not elastic, or highly retractable) in the cross direction. Thus, when the laminate is stretched in the cross direction, the film is stretched, and the nonwoven web returns toward its original, un-necked state. The stretched laminate exhibits little or no retractive force after being held for one minute in the stretched condition. In this embodiment, the laminate has cross-directional extendibility but may not have machine direction extendibility if the nonwoven web is made from a non-extendible polymer composition.

In another embodiment, the thermoplastic nonwoven web is not necessarily neck-stretched, but is made using an extendible (but not elastic, or highly retractable) polymer material. The film also includes at least one thermoplastic polymer which renders the film extendible (but not elastic, or highly retractable) in the cross direction. When the laminate is stretched in the cross direction, the film is stretched, and the fibers in the nonwoven web are also stretched. The stretched laminate exhibits little or no retractive force. In this embodiment, the laminate may have extendibility in the machine direction as well as the cross direction, since both the film and web are made from extendible polymers.

In another embodiment, the thermoplastic web is not necessarily neck-stretched or made using a stretchable polymer. Instead, the nonwoven web is rendered stretchable by crimping of the filaments. Crimped filaments have undulations and/or spirals along their length which tend to straighten out when a stretching force is applied, thus rendering the filaments elongatable. Again, the film includes at least one thermoplastic polymer which renders the film stretchable (but not elastic, or highly retractable) in the cross direction. When the laminate is stretched in the cross direction, the film is stretched, and the crimped filaments of the nonwoven web tend to straighten out. Again, the stretched laminate exhibits little or no retractive force. In this embodiment, the laminate may have extendibility in the machine direction as well as the cross direction, since the film is made from an extendible polymer and the web will extend in either direction.

In yet another embodiment, the thermoplastic nonwoven web is partially necked, or extended, to, e.g., one half of its machine direction extension capacity. An extendible polymer film, such as a flexible polyolefin (FPO) or other soft polymer film, is also preferably, but not necessarily, stretched in the machine direction. The laminate is then made by bonding the partially stretched nonwoven web and the preferably, but not necessarily, partially stretched film. The laminate then undergoes another stretching in the machine direction, thus creating and setting rugae, or wrinkles, in the film portion of the laminate. When the stretched laminate is then tensioned in the cross direction the rugae of the film flatten out easily with very little tensioning force providing extension of the laminate in the cross direction. It will be recognized that while "easily" is a relative term, in this general context it will apply to that amount of tensioning force normally asserted by application to the body of the wearer of a finished garment utilizing the laminate. A second higher force is then needed to achieve additional cross direction extension through stretching to thin the film in the cross direction beyond the point where the rugae have completely flattened out. Again, the stretched laminate exhibits little or no retractive force. With this embodiment, the extendibility force profile of the resultant laminate may be variously adjusted at either the pre-lamination or post-lamination extension procedures, or both.

With the foregoing in mind, it is a feature and advantage of the invention to provide a substantially liquid-impermeable (preferably breathable) laminate which stretches where needed, and exhibits little retractive force, thereby conforming permanently to the contour of a wearer's body.

It is also a feature and advantage of the invention to provide a laminate which conforms to the contours of a wearer's body, and which is relatively inexpensive to manufacture compared to prior art elastic laminates.

It is also a feature and advantage of the invention to provide various personal care and medical garments which incorporate the breathable laminate of the invention, and which (due to their extendibility and low retractions) permanently conform to the contour of a wearer's body.

The foregoing and other features and advantages will become further apparent from the following detailed description of the presently preferred embodiments, read in conjunction with the accompanying drawings. The detailed description and drawings are intended to be illustrative rather than limiting, the scope of the invention being defined by the appended claims and equivalents thereof.

Definitions

The term "extendible" is used herein to mean a material which upon application of a stretching force, can be extended in a particular direction, to a stretched dimension (e.g., width) which is at least 25% greater than an original, unstretched dimension. When the stretching force is removed after a one-minute holding period, the material does not retract, or retracts by not more than 30% of the difference between the stretched dimension and the original dimension. Thus, a material having a width of one meter, which is extendible in the cross direction, can be stretched to a width of at least 1.25 meters. When the stretching force is released, after holding the extended width for one minute, a material stretched to a width of 1.25 meters will not retract, or will retract to a width of not less than 1.175 meters. Extendible materials are different from elastic materials, the latter tending to retract most of the way to their original dimension when a stretching force is released. The stretching force can be any force sufficient to extend the material to between 125% of its original dimension, and its maximum stretched dimension in the selected direction (e.g., the cross direction) without rupturing it.

The "percent retraction" is determined when the retractive force drops below 10 grams for a 3-inch wide sample, using the procedure set forth in the Examples. "Percent permanent set" is 100 minus "percent retraction."

The term "inelastic" refers both to materials that do not stretch by 25% or more and to materials that stretch by that amount but do not retract by more than 30%. Inelastic materials include extendible materials, as defined above, as well as materials that do not extend, e.g., which tear when subjected to a stretching force.

The term "machine direction" as applied to a nonwoven web, refers to the direction of travel of a conveyor passing beneath the spinnerette or similar extrusion or forming apparatus for the filaments, which causes the filaments to have primary orientation in the same direction. While the filaments may appear wavy, or even randomly oriented in a localized section of a nonwoven web, they usually have an overall machine direction of orientation which was parallel to the movement of the conveyor that carried them away from the extrusion or forming apparatus.

The term "machine direction" as applied to a film, refers to the direction on the film that was parallel to the direction of travel of the film as it left the extrusion or forming apparatus. If the film passed between nip rollers or chill rollers, for instance, the machine direction is the direction on the film that was parallel to the surface movement of the rollers when in contact with the film.

The term "machine direction" as applied to a laminate including at least one film and at least one nonwoven web, refers to the machine direction of the nonwoven web component of the laminate.

The term "cross direction" for a nonwoven web, film, or laminate refers to the direction perpendicular to the machine direction. Dimensions measured in the cross direction are referred to as "width" dimensions, while dimensions measured in the machine direction are referred to as "length" dimensions.

The terms "breathable film," "breathable laminate" or "breathable outer cover material" refer to a film, laminate, or outer cover material having a water vapor transmission rate ("WVTR") of at least about 300 grams/m$^2$-24 hours, using the WVTR Test Procedure described herein. The term "higher breathability" simply means that a second material has a higher WVTR than a first material. Breathable materials typically rely on molecular diffusion of vapor, or vapor passage through micropores, and are substantially liquid impermeable.

The term "liquid water-permeable material" refers to a material present in one or more layers, such as a nonwoven fabric, which is porous, and which is liquid water permeable due to the flow of water and other aqueous liquids through the pores. The spaces between fibers or filaments in a nonwoven web can be large enough and frequent enough to permit leakage and flow of liquid water through the material.

The term "nonwoven fabric or web" means a web having a structure of individual fibers or threads which are interlaid, but not in a regular or identifiable manner as in a knitted fabric. Nonwoven fabrics or webs have been formed from many processes such as, for example, meltblowing processes, spunbonding processes, air laying processes, coforming processes, and bonded carded web processes. The basis weight of nonwoven fabrics is usually expressed in ounces of material per square yard (osy) or grams per square meter (gsm) and the fiber diameters useful are usually expressed in microns. (Note that to convert from osy to gsm, multiply osy by 33.91.)

The term "microfibers" means small diameter fibers typically having an average fiber denier of about 0.005–10. Fiber denier is defined as grams per 9000 meters of a fiber. For a fiber having circular cross-section, denier may be calculated as fiber diameter in microns squared, multiplied by the density in grams/cc, multiplied by 0.00707. For fibers made of the same polymer, a lower denier indicates a finer fiber and a higher denier indicates a thicker or heavier fiber. For example, the diameter of a polypropylene fiber given as 15 microns may be converted to denier by squaring, multiplying the result by 0.89 g/cc and multiplying by 0.00707. Thus, a 15 micron polypropylene fiber has a denier of about 1.42 calculated as ($15^2$×0.89×0.00707=1.415). Outside the United States the unit of measurement is more commonly the "tex," which is defined as the grams per kilometer of fiber. Tex may be calculated as denier/9.

The term "spunbonded fibers" refers to small diameter fibers which are formed by extruding molten thermoplastic material as filaments from a plurality of fine capillaries of a spinnerette having a circular or other configuration, with the diameter of the extruded filaments then being rapidly reduced as by, for example, in U.S. Pat. No. 4,340,563 to Appel et al., and U.S. Pat. No. 3,692,618 to Dorschner et al., U.S. Pat. Nos. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Petersen, and U.S. Pat. No. 3,542,615 to Dobo et al., each of which is incorporated herein in its entirety by reference. Spunbond fibers are quenched and generally not tacky when they are deposited onto a collecting surface. Spunbond fibers are generally continuous and often have average deniers larger than about 0.3, more particularly, between about 0.6 and 10.

The term "meltblown fibers" means fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed for example, in U.S. Pat. No. 3,849,241 to Butin et al. Meltblown fibers are microfibers which may be continuous or discontinuous, are generally smaller than about 1.0 denier, and are generally self bonding when deposited onto a collecting surface.

The term "film" refers to a thermoplastic film made using a film extrusion process, such as a cast film or blown film extrusion process. This term includes films rendered microporous by mixing polymer with filler, forming a film from the mixture, and stretching the film.

The term "microporous" refers to films having voids separated by thin polymer membranes and films having micropores passing through the films. The voids or micropores can be formed when a mixture of polymer and filler is extruded into a film and the film is stretched, preferably uniaxially in the machine direction. Microporous films tend to have water vapor transmission due to molecular diffusion of water vapor through the membranes or micropores, but substantially block the passage of aqueous liquids.

The term "polymer" includes, but is not limited to, homopolymers, copolymers, such as for example, block, graft, random and alternating copolymers, terpolymers, etc. and blends and modifications thereof. Furthermore, unless otherwise specifically limited, the term "polymer" shall include all possible geometrical configurations of the material. These configurations include, but are not limited to isotactic, syndiotactic and atactic symmetries.

The term "absorbent article" includes personal care absorbent products and medical absorbent products. The term "personal care absorbent product" includes without limitation diapers, training pants, swim wear, absorbent underpants, baby wipes, adult incontinence products, and feminine hygiene products.

The term "medical absorbent product" includes without limitation absorbent garments, underpads, bandages, face masks, absorbent drapes, and medical wipes.

The term "neck" or "neck stretch" interchangeably means that the fabric, nonwoven web or laminate is drawn such that it is extended under conditions reducing its width or its transverse dimension by stretching lengthwise or increasing the length of the fabric. The controlled drawing may take place under cool temperatures, room temperature or greater temperatures and is limited to an increase in overall dimension in the direction being drawn up to the elongation required to break the fabric, nonwoven web or laminate, which in most cases is about 1.2 to 1.6 times. When relaxed, the fabric, nonwoven web or laminate does not return totally to its original dimensions. The necking process typically involves unwinding a sheet from a supply roll and passing it through a brake nip roll assembly driven at a given linear speed. A take-up roll or nip, operating at a linear speed higher than the brake nip roll, draws the fabric and generates the tension needed to elongate and neck the fabric. U.S. Pat. No. 4,965,122 issued to Morman, and commonly assigned to the assignee of the present invention, discloses a reversibly necked nonwoven material which may be formed by necking the material, then heating the necked material, followed by cooling and is incorporated herein by reference in its entirety. The heating of the necked material causes additional crystallization of the polymer giving it a partial heat set. If the necked material is a spunbond web, some of the fibers in the web may become crimped during the necking process, as explained in U.S. Pat. No. 4,965,122.

The term "neckable material" or "neckable layer" means any material or layer which can be necked such as a nonwoven, woven, or knitted material, or a laminate containing one of them. As used herein, the term "necked material" refers to any material which has been drawn in at least one dimension, (e.g., lengthwise), reducing the transverse dimension, (e.g., width), such that when the drawing force is removed, the material can be pulled back to its original width. The necked material generally has a higher basis weight per unit area than the un-necked material. When the necked material is pulled back to its original width, it should have about the same basis weight as the un-necked material. This differs from stretching/orienting the film layer, during which the film is thinned and the basis weight is reduced. Preferred nonwoven webs for use in the invention are made from an inelastic polymer.

The term "percent neckdown" refers to the ratio determined by measuring the difference between the un-necked dimension and the necked dimension of the neckable material and then dividing that difference by the un-necked dimension of the neckable material.

DETAILED DESCRIPTION OF THE PRESENTLY PREFERRED EMBODIMENTS

Figure 1:
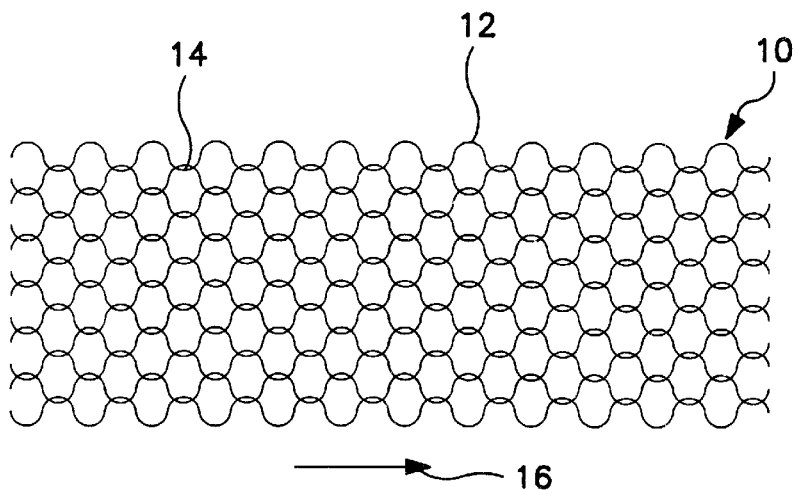
FIG. 1 illustrates a top view of a fibrous nonwoven web, which can be a spunbond web, which has not been necked.

Referring to FIG. 1, a nonwoven web 10, which can be a spunbond web, includes a plurality of individual thermoplastic fiber elements 12 intermittently bonded together using a bonding pattern which, in this instance, includes a plurality of point bonds 14. The individual fibers 12 appear to have a wavy or somewhat random orientation when viewed on a microscopic scale. When viewed on a microscopic scale, so that the entire lengths of fibers 12 are visible, the fibers 12 have an overall primary direction of orientation which is parallel to a machine direction, represented by arrow 16. If the nonwoven web is spunbond, it may be intentionally produced with high machine-direction filament orientation and thermal bonds oriented predominantly in the machine direction. This will provide the spunbond web with inherent cross-directional extendibility, much like that existing in a conventional bonded carded web.

Figure 2:
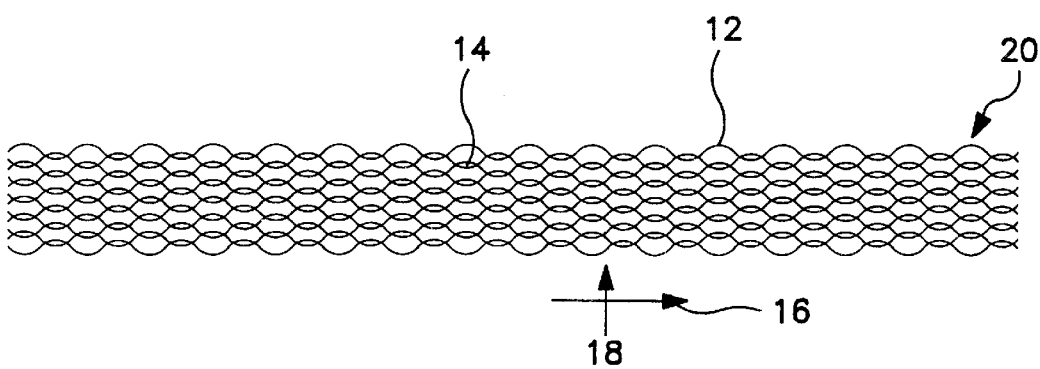
FIG. 2 illustrates a top view of a fibrous nonwoven web, which can be a spunbond web, which has been necked.

The nonwoven web 10 is preferably a spunbond web, but can also be a meltblown web, a bonded carded web, an air laid web, or a laminate or composite including one or more nonwoven webs. The nonwoven web may also be formed or modified using a hydraulic entangling process. In one embodiment of the invention, the nonwoven web or laminate including it, is neckable, as defined above. FIG. 2 illustrates a top view of a necked nonwoven material 20, which can be the nonwoven web 10 stretched in the machine direction 16 to cause elongation of the web in the machine direction 16 and narrowing, or neck-in, in the cross direction 18. As shown in FIG. 2, necking causes the individual filaments 12 to become more aligned with each other, and closer to each other. When a neckable nonwoven web or laminate is employed, it should have a percent neck-down of at least about 15%, more preferably about 25–75%, most preferably about 35–65%. Prior to necking, the nonwoven web 10 should have a basis weight of about 0.05–4.0 ounces per square yard. ("osy"), preferably about 0.3–2.0 osy, more preferably about 0.4–1.0 osy.

When a neckable nonwoven web is used, the nonwoven web can be constructed from either a non-extendible or an extendible polymer. Examples of suitable non-extendible polymers include, without limitation, polyolefins, polyamides, and polyesters. Preferred polymers include polyolefins, such as polypropylene and/or polyethylene. Other suitable polymers include copolymers of mainly ethylene and $C_3$–$C_{12}$ alpha-olefins, having a density of about 0.900–0.935 grams 1 $cm^3$, commonly known as linear low density polyethylenes. Also included are copolymers of at least 90% by weight propylene with not more than 10% by weight $C_2$ or $C_4$–$C_{12}$ alpha-olefins. Extendible polymers (as described below), which are preferred when the nonwoven web 10 is not neck-stretched or the fibers crimped, may also be used when it is neck-stretched. Single-site catalyzed polyolefins (i.e., metallocene-catalyzed or constrained geometry-catalyzed) are also useful. These polyolefins may be extendible or not extendible, depending on their density and monomer content. Single-site catalyzed polyolefins are described in U.S. Pat. Nos. 5,571,619; 5,322,728; and 5,272,236, the disclosures of which are incorporated by reference.

Polymers made using single-site catalysts have a very narrow molecular weight range. Polydispersity numbers (Mw/Mn) of below 4 and even below 2 are possible for metallocene-produced polymers. These polymers also have a controlled short chain branching distribution compared to otherwise similar Ziegler-Natta produced type polymers. It is also possible using a metallocene catalyst system to control the isotacticity of the polymer quite closely. In general, polyethylene polymers and copolymers having a density of 0.900 grams/cc or greater tend to be less extendible or not extendible, while those having a density below 0.900 grams/cc are more extendible. In general, polypropylene polymers and copolymers containing 0–10% of an ethylene or other alpha-olefin comonomer tend to be less extendible or not extendible, while propylene-alpha olefin copolymers containing more than 10% comonomer are more extendible.

Commercial production of single-site catalyzed polymers is somewhat limited but growing. Such polymers are available from Exxon Chemical Company of Baytown, Tex. under the trade name ACHIEVE for polypropylene based polymers and EXACT and EXCEED for polyethylene based polymers. Dow Chemical Company of Midland, Mich. has polymers commercially available under the name AFFIN- ITY. These materials are believed to be produced using non-stereo selective metallocene catalysts. Exxon generally refers to their catalyst technology as single site or metallocene catalysts while Dow refers to theirs as "constrained geometry" catalysts under the name INSITE to distinguish them from traditional Ziegler-Natta catalysts which have multiple reaction sites. Other manufacturers such as Fina Oil, BASF, Amoco, Hoechst and Mobil are active in this area and it is believed that the availability of polymers produced according to this technology will grow substantially in the next decade.

In a second embodiment, the cross direction extendible nonwoven web 10 is not neck-stretched. In this embodiment, the nonwoven web 10 is made from an extendible polymer material, i.e., one which permits the individual fibers 12 to stretch by at least 25% of their initial length, and not retract by more than 30% of the difference between the stretched length and the unstretched length when a stretching force is removed. Preferably, the extendible polymer is one which permits the individual fibers 12 to stretch by at least 35% (e.g., 35–300%) of their initial length, and not retract by more than 30% of the difference between the stretched and unstretched lengths when the stretching force is removed. More preferably, the extendible polymer permits the individual fibers 12 to stretch by at least 50% (e.g., 50–200%) of their initial, unstretched length and not retract more than 30% of said difference. The extendible fibers 12 may be composed of a blend or other combination of an extendible and non-extendible polymer, so long as the extendible polymer is present in sufficient quantity to render the fibers extendible.

Examples of extendible polymers include certain flexible polyolefins, for example propylene-based polymers having both atactic and isotactic propylene groups in the main polypropylene chain. Flexible polyolefins (FPO's) are sold by the Rexene Corporation. Also included are heterophasic propylene-ethylene copolymers sold as "catalloys" by the Himont Corporation. Heterophasic polymers are reactor blends formed by adding different levels of propylene and ethylene at different stages in the reactor. Heterophasic polymers typically include about 10–90% by weight of a first polymer segment A, about 10–90% by weight of a second polymer segment B, and 0–20% by weight of a third polymer segment C. Polymer segment A is at least about 80% crystalline and includes about 90–100% by weight propylene, as a homopolymer or random copolymer with up to 10% by weight ethylene. Polymer segment B is less than about 50% crystalline, and includes about 30–70% by weight propylene randomly copolymerized with about 30–70% by weight ethylene. Optional polymer segment C contains about 80–100% by weight ethylene and 0–20% of randomly copolymerized propylene.

Other extendible polymers include very low density polyethylene (VLDPE), which is an ethylene-alpha olefin copolymer having a density less than 0.900 grams/cm$^3$, preferably about 0.870–0.890 grams/cm$^3$. Preferred VLDPE's are single-site catalyzed. Other extendible polymers include random propylene-alpha olefin copolymers containing more than 10% by weight of a $C_2$ or $C_4$–$C_{12}$ comonomer, preferably about 15–85% by weight of the comonomer, with ethylene being a preferred comonomer.

In a third embodiment, the cross direction extendible nonwoven web 10 is made of fibers 12 that are crimped. A wide variety of crimping processes are known in the art. Crimped fibers have accordion-like or spring-like undulations or microundulations so that when the fibers are extended, they straighten out and/or the undulations are reduced in amplitude. When crimped fibers are used, the polymer of construction need not be extendible, i.e., may be extendible or not extendible.

In yet another embodiment, the nonwoven is formed so that the fibers have very high machine direction (MD) and very little cross direction (CD) orientation. The fibers are then bonded so as to minimize CD bonding of the fibers. This allows the material to be extended in the CD. An example of such a material is a bonded carded web (BCW) nonwoven that has high CD extendibility and low MD extendibility. Other nonwovens, such as spunbonds, can be made to perform like BCW's by forming the spunbond fibers so that the fibers are highly oriented in the MD and bond the filaments with a bond pattern so that the material can readily extend in the CD. Such a bond pattern would have lower percent bond area (less than 25%) with the bonds lined up predominately in the MD. Thus there are columns of fibers in the MD which are not bonded adjacent to columns of fibers in the MD that are. The unbonded fibers allow the nonwoven to readily extend in the CD while the bonded fibers give the material strength and abrasion resistance. BCW materials are described further in *Encyclopedia of Polymer Science and Engineering,* Vol. 10, Pages 211–212, Wiley & Sons (1987), which is incorporated by reference.

Figure 3:
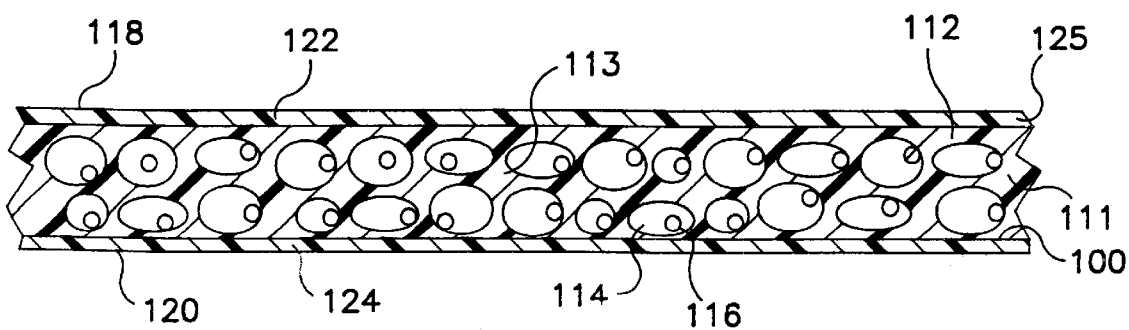
FIG. 3 illustrates a sectional view of a breathable microporous film which can be laminated to the nonwoven web of FIG. 1 or FIG. 2.

FIG. 3, illustrates one embodiment of an extendible film, in this case a breathable extendible microporous film, that can be laminated to the neck-stretched nonwoven web of the first embodiment, the extendible polymer-based nonwoven web of the second embodiment, or the crimped nonwoven web of the third embodiment. The breathable microporous film 100 can include a primary microporous core layer 112, sandwiched between two thinner skin layers 122 and 124 which are used for bonding. Alternatively, the film 100 may include a primary microporous core layer 112, and only one skin layer 122 or 124, or no skin layers.

The microporous layer 112 includes a polymer matrix 111, a plurality of voids 114 within the matrix surrounded by relatively thin microporous membranes 113 defining tortuous paths, and one or more filler particles 116 in each void 114. The layer 112 is microporous and breathable, wherein the microporous membranes 113 between the voids readily permit molecular diffusion of water vapor from a first surface 118 to a second surface 120 of the film 100. Alternatively, some or all of the micropores can pass through the film, or can be interconnected to provide through-passages.

The polymer matrix 111 can be formed from any extendible film-forming thermoplastic polymer. Examples of suitable polymers include without limitation any one or more of the extendible polymers named above for the second embodiment of the nonwoven web having extendible fibers. The extendible polymer should be of a type and amount that causes the film 100 to have cross-directional extendibility of at least about 25% of an initial, unstretched width when a stretching force is applied. When the stretching force is relaxed, the film should not retract by more than 30% of the difference between the stretched width and the initial, unstretched width. Preferably, film 100 should have cross-directional extendibility of at least about 35% (e.g., 35–300%) of the initial width, more preferably at least about 50% (e.g., 50–200%). The extendible polymer may be blended with a non-extendible polymer so long as the film has the needed extendibility. Preferred polymers for the matrix 111 are single-site catalyzed ethylene copolymers and flexible polyolefins (FPOs) as described above.

The filler particles 116 can include any suitable inorganic or organic filler. The filler particles 116 are preferably small to produce micropores, in order to maintain liquid water barrier of the film 100. Generally, the filler particles should have a mean particle diameter of about 0.1–7.0 microns, preferably about 0.5–5.0 microns, most preferably about 0.8–2.0 microns. Suitable fillers include without limitation calcium carbonate, non-swellable clays, silica, alumina, barium sulfate, sodium carbonate, talc, magnesium sulfate, titanium dioxide, zeolites, aluminum sulfate, diatomaceous earth, magnesium sulfate, magnesium carbonate, barium carbonate, kaolin, mica, carbon, calcium oxide, magnesium oxide, aluminum hydroxide and polymer particles. Calcium carbonate is a presently preferred filler.

The filler particles 116 may be coated with a minor quantity (e.g., up to 2% by weight) of a fatty acid or other material to ease their dispersion in the polymer matrix. Suitable fatty acids include without limitation stearic acid, or a larger chain fatty acid such as behenic acid. The amount of filler particles 116 in the core layer 112 of the film 100 should range from about 10–55% by total (polymer and filler) volume of the layer 112, preferably about 15–45% by volume, most preferably about 25–40% by volume. Similarly, the polymer matrix 111 should constitute about 45–90% by volume of the core layer 112, preferably about 55–85% by volume, more preferably about 60–75% by volume. The term "volume" refers to the total volume occupied by polymer and filler, and excludes air space in the voids or micropores.

The polymer composition, filler content, filler particle size and degree of stretching are factors which help determine the breathability and liquid barrier of the extendible microporous film 100 in the laminate. Generally, the oriented microporous film 100 will be less than about 50 microns thick, preferably less than about 30 microns thick, most preferably less than about 20 microns thick. The film 100 may be uniaxially stretched to about 1.1–7.0 times its original length to cause breathability, preferably to about 1.5–6.0 times its original length, most preferably to about 2.5–5.0 times its original length. The film may alternatively be biaxially stretched using conventional techniques familiar to persons skilled in the art. Preferably, the film is uniaxially stretched in its machine direction, and is laminated to the nonwoven web with the machine direction of the film aligned with the machine direction of the web. Stretching temperatures may range from about 38–150° C. depending on the specific polymers employed, and are preferably about 70–95° C. The breathable extendible film 100 can be prepared by cast or blown film coextrusion of the layers, by extrusion coating, or by any conventional layering process.

In the embodiment of FIG. 3, the microporous breathable film layer 112 is adjacent one or two relatively thin outer skin layers 122 and 124, in a two or three-layer extendible film 100. The inclusion of one or two skin layers improves film processability and can also contribute heat seal properties to the breathable extendible film 100. The polymers in the outer layers 122 and 124 can be the same or different than the polymers in the microporous layer 112. Preferably, the polymers in the outer layer or layers are extendible, have a lower softening point than in the microporous layer 112, and contribute to the heat sealability of the film 100. To facilitate breathability, the skin layers 122 and 124 may contain a particulate filler in any quantity up to the same amount as the microporous core layer 112, and the skin layers may be microporous as well after the film is oriented.

Also, the thickness and composition of the outer layers 122 and 124 should be selected so as not to substantially impair the moisture transmission through the breathable film 100. This way, the microporous core layer 112 may determine the breathability of the entire film. To this end, the skin layer 122 and 124 is generally less than about 10 microns thick, preferably less than about 5 microns thick. The combined skin layers should constitute no more than 25% of the entire film thickness, and preferably constitute about 2–15% of the film thickness, more preferably 3–5% of the total film thickness. Preferred extendible skin layer polymers having low softening points include amorphous metallocene or Ziegler Natta-catalyzed copolymers of ethylene with a $C_3$–$C_{20}$ alpha-olefin comonomer, having a density less than about 0.89 grams/cc. Also suitable are amorphous poly alpha-olefin (APAO) polymers which can be random copolymers or terpolymers of ethylene, propylene, and butene, and other substantially amorphous or semi-crystalline propylene-ethylene polymers. Also included are ethylene vinyl acetates, propylene vinyl acetates, ethylene methyl acrylates, and blends of any of the foregoing polymers.

The cross direction extendible microporous film 100 should have a water vapor transmission rate ("WVTR") of at least 300 grams/$m^2$-24 hours, measured using the procedure described below. Preferably, film 100 should have a WVTR of at least 1200 grams/$m^2$-24 hours, more preferably at least 2000 grams/$m^2$-24 hours.

Figure 4:
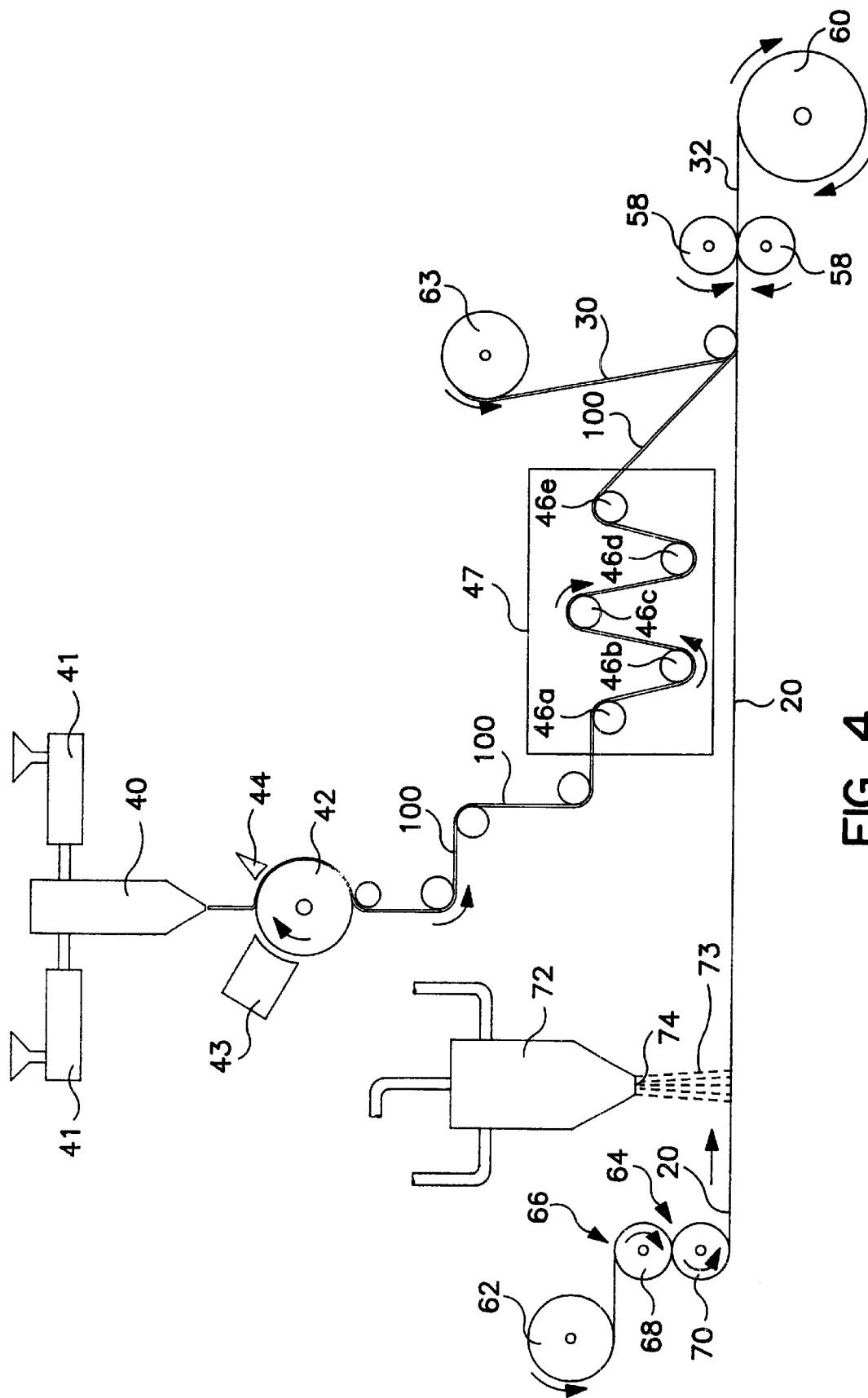
FIG. 4 schematically illustrates a process that can be used to form the breathable laminates of the invention.

FIG. 4 illustrates an integrated process for forming a multilayer breathable film and a laminate. Referring to FIG. 4, film 100 is formed from a film coextrusion apparatus 40 such as a cast or blown unit which could be in-line or off-line. Typically the apparatus 40 will include two or three extruders 41. To make the core layer, filled resin including the polymer matrix material and filler is prepared in a mixer (not shown) and directed to an extruder 41. To make each skin layer, similar additional mixing apparatus (not shown) and extrusion apparatus 41 can be used to mix the incompatible polymer components and extrude them as skin layers on one or both sides of the core layers. The multilayer film 100 is extruded onto a chill roller 42, which cools the film 100. A vacuum box 43 adjacent the chill roller creates a vacuum on the surface of the chill roller to help maintain the film close to the surface of the chill roller. Air knives or electrostatic pinners 44 also urge the film 100 against the roller surface.

From the film extrusion apparatus 40 or off-line rolls supplied, the multilayer film 100 is directed to a film stretching unit 47 which can be a machine direction orienter, commercially available from vendors including the Marshall and Williams Co. of Providence, R.I. Apparatus 47 has a plurality of stretching rollers 46a–e, which progressively stretch and thin the film in the machine direction, which is the direction of travel of the film. The rollers 46a–e, which are heated to the desired stretching temperature, apply an amount of stress and progressively stretch the multilayer film 100 to a stretched length where the core layer 112 becomes microporous and breathable, and the skin layers 122 and 124 become sufficiently thin, and perhaps microporous, so as not to inhibit overall film breathability. While the apparatus 47 is shown with five stretching rollers 46a–e, the number of rollers may be greater or less depending on the level of stretch desired and the amount of stretching between each pair of rollers. In one of the preferred embodiments, the rollers will be set to achieve an extension of between 100% to 500% of the film to make it breathable. If, for example, the film is being run at 100 ft/min, the stretch rollers will be run at 450 ft/min for a 350% stretch. If breathability is not desired the film need not be stretched.

Advantageously, the film 100 may be uniaxially stretched to about 1.1–7.0 times its original length, preferably about 1.5–6 times its original length, suitably about 2.5–5 times its original length, using an elevated stretch temperature as explained above. The elevated stretch temperature can be sustained by heating some or all of the stretch rollers 46*a–e*. The optimum stretch temperature varies with the core layer and skin layer polymers of film 100, and is generally below the melting temperature of the matrix polymer in the core layer 112.

The multilayer film 100 may be laminated to one or more substrates, such as a nonwoven web, using conventional adhesive bonding or thermal bonding techniques known in the art. The type of substrate and bonding will vary depending on the particular end use application. Referring again to FIG. 4, film 100 may be laminated to nonwoven web 20 immediately after the film is stretched. In one embodiment, a neckable nonwoven web 20, which can be a spunbond web, is unwound from a supply roll 62. The neckable material 20 then passes through the nip 64 of S-roll arrangement 66, formed by a stack of rollers 68–70, in a reverse S-wrap path as shown by the arrows. Rollers 68 and 70 turn at a slower circumferential speed than downstream calender bonding rollers 58, causing tensioning and neck-in of web 20. In one of the preferred embodiments, the rollers will be set to achieve an extension of about 12.5% of the extendibility, or necking limit, of the web as a prelamination extension in the machine direction. If, for example, the web is being run at 400 ft/min the stretch rollers will be run at 450 ft/min to initially neck the web. The tensioned, necked material can be passed under spray equipment 72 (e.g., a meltblown die) which sprays adhesive 73 through die head 74 onto a surface of web 20. With or without the adhesive treatment, the necked web 20 can then be joined to multilayer film 100, and bonded between calender rollers 58, which can be heated if necessary. The film 100 in FIG. 4 is simultaneously bonded on its other side to a second material 30 originating from supply roll 63. The second extendible material 30 may be a second nonwoven web, or another film layer. The resulting laminate 32 is wound and stored on a supply roll 60. In addition to the described bonding technique, other bonding techniques (e.g., other thermal, adhesive or ultrasonic bonding) may be employed.

In another preferred embodiment, a spunbond is machine direction stretched to neck a spunbond web. The necked spunbond is laminated to a cross direction extendable, but not extended, film. The laminate is then stretched in the machine direction to neck the laminate. The last stretching step elongates and thins the film, but does not appreciably neck it. However, the spunbond does neck and forces the attached film to narrow with it. This forced narrowing causes rugae or corrugates to form in the film. It is thought that additional crystallization is occurring in the rugae during this drawing/stretching step which produces memory in the film to stay in the corrugated, narrowed configuration. A gentle cross direction force will cause the rugae to extend and thus the laminate has easy cross direction extendability to the width at which the laminate was formed. At this width, the spunbond can still extend to its original, pre-necked width but the film must actually be extended which requires more force than just pulling out the rugae.

By adjusting the pre-lamination and post lamination stretching/necking steps, a laminate with the desired amount of easy and harder stretch can be made. This is very useful to make a product that readily and easily extends in the cross direction to fit the wearer but has additional "elongation" in reserve so the product can extend without tearing.

If it was desired to have a microporous breathable film in the laminate, a filled film will have been used and stretched enough before laminating such that the post laminating stretching step will have produced enough total stretch to make it breathable.

Figure 5:
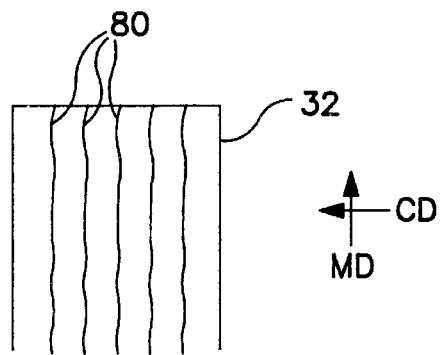
FIG. 5 illustrates a top view of a extendible film which has been extended to set rugae therein.
Figure 6:
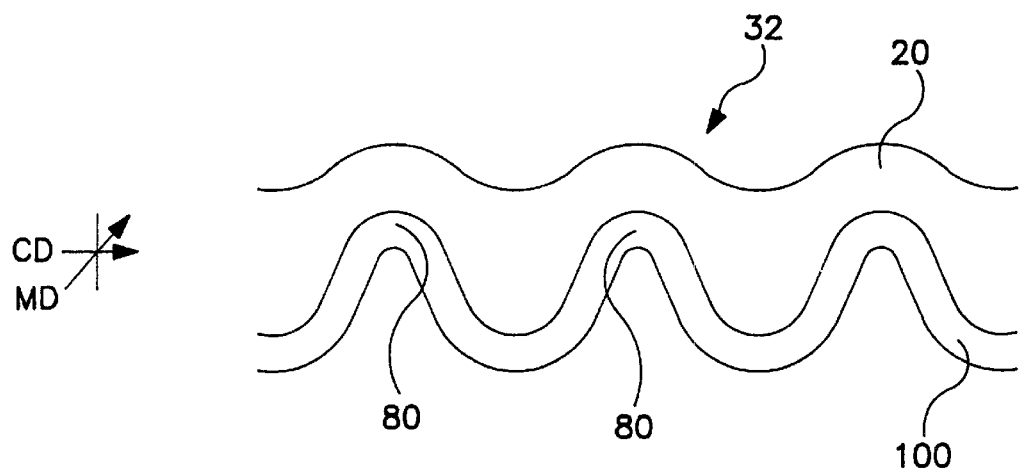
FIG. 6 illustrates a sectional view of the laminate taken along the cross direction and showing the rugae therein.

In the embodiment of the partially necked web and stretched film components, the supply roll 60, or additional tensioning rolls (not shown) located prior to the supply roll 60 but after calendaring rolls 58, will be used to perform additional extension of the laminate 32. It is important to give the laminate enough time/distance to narrow in. The drawing should therefore not be considered as being in-scale. Referencing FIG. 5, this additional extension will form or set, or both, the rugae 80 in the film 100 and further extend and neck the nonwoven web 20 and thus narrow the laminate 32. This final stretching may be about another 11% stretch of the laminate or up to the extension limit of the web material in its machine direction.

The desired cross-directional extendibility of laminate 32 is preferably achieved by aligning extendible breathable film 100 with the cross direction extendible webs 20 and 30, so that both are traveling in their respective machine directions during bonding, and the machine directions of the film and web are substantially parallel to each other. If the nonwoven web 20 is a necked web, the cross-directional extendibility of the laminate is achieved by returning the web toward its initial, un-necked state as the film and web are extended in the cross direction. If the nonwoven web is not necked but made of an extendible polymer, then its fibers are extended as the film is extended in the cross direction. If the nonwoven web is made from crimped fibers, then its fibers merely become less crimped or un-crimped as the film is extended in the cross direction. The fibers can be both crimped and made from an extendible polymer, or present in a bonded carded web. Because the breathable film has already been stretched in its machine direction prior to lamination, the film has a greater tendency to extend in the cross direction after lamination, than to extend further in the machine direction.

Figure 7:
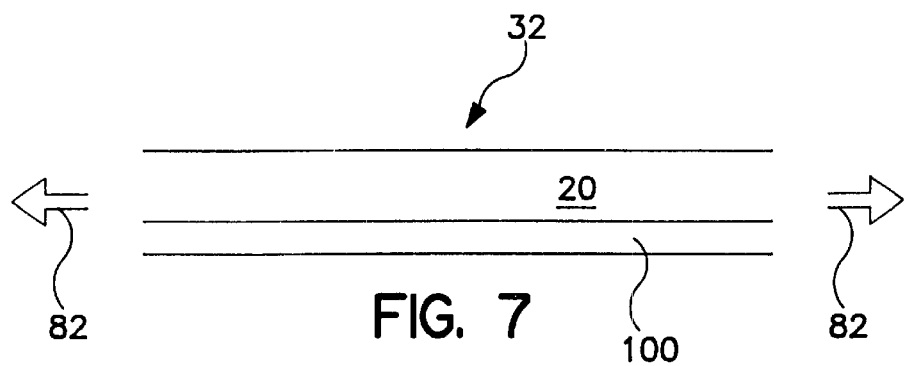
FIG. 7 illustrates an application of tensioning force to the laminate of FIG. 6 showing a cross direction extension through a flattening of the rugae.
Figure 8:
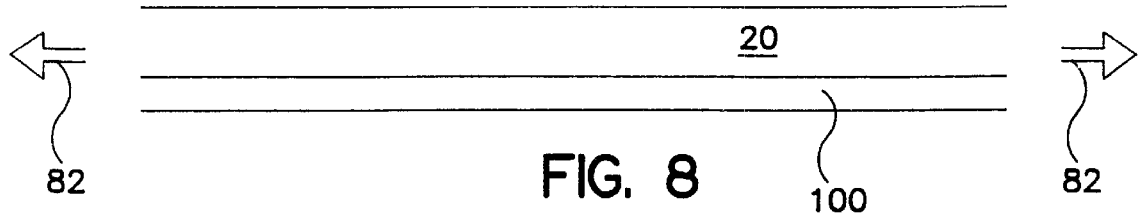
FIG. 8 illustrates an application of tensioning force to the flattened laminate of FIG. 7 showing additional cross direction extension through a stretching of the film of the laminate.

Referencing FIGS. 5–8, if the laminate 32 is made from a partially-necked web and partially extended film which are then more completely stretched after lamination, the cross-directional extendibility of the laminate is achieved by an unfolding, or flattening, of the rugae 80 in the film 100 and a returning of the web 20 toward its initial, un-necked state in the cross direction, as seen in FIG. 7, through the application of a tensioning force as indicated by arrows 82. Then a second extendibility with higher force as indicated by arrows 84, is achieved as the film 100 is stretched and thinned beyond the limits of the rugae unfolding, as seen in FIG. 8.

The overall laminate 32 has cross-directional extendibility influenced by the extendabilities of the film and nonwoven web. Specifically, the laminate has a cross-directional extendibility of at least 25% of its initial width, preferably at least 35% of its initial width, more preferably at least 50% of its initial width when a stretching force is applied, without rupturing the laminate. When the stretching force is removed, the laminate does not recover or retract by more than 30% of the difference between the fully stretched width and the original width after a one-minute holding period.

Another way to characterize the laminate of the invention, is in terms of the percent drop in retractive force experienced during a one-minute holding period in the stretched condition. The procedure for measuring the percent drop in retractive force is set forth below in the Examples. Briefly, a sample of the laminate material is extended in the cross direction by 50% of its initial width. The retractive force is measured immediately after extending the material by 50%, and after a one-minute holding period in the extended condition. The percent force drop is calculated as:

$$\% \text{ force drop} = 100 \times \left[ \frac{\text{retractive force (time = 0)} - \text{retractive force (time = 60 sec)}}{\text{retractive force (time = 0)}} \right]$$

To stay within the limited retraction required by the invention, the laminate should exibit a percentage force drop of at least about 35%, preferably at least about 45%.

The cross direction extendible, breathable laminate may be used in a wide variety of personal care absorbent articles and medical articles. Absorbent articles include without limitation diapers, training pants, swim wear, absorbent underpants, adult incontinence products, feminine hygiene products, and the like. Medical products include medical garments, face masks, underpads, bandages, drapes, medical wipes, and the like.

The cross direction extendible, breathable laminate has the advantage of being selectively extended only in regions where stretching is needed, to conform to the contours of a wearer's body. For example, a diaper or pant-like absorbent garment embodying the laminate as an outercover can be made smaller, using less material than a diaper that is not stretchable. When the absorbent garment is applied to a wearer, it stretches in the cross direction only where needed (for example, in the front and back of the wearer) to ensure a perfect fit. Because retractive forces are minimal, the problem of skin marks and rashes occurring in the regions of greatest stretch is substantially overcome.

WVTR Test Procedure

The following procedure is described for testing of the water vapor transmission rate (WVTR) for the films of the invention. The WVTR is measured in a manner similar to ASTM Standard Test Method for Water Vapor Transmission of Materials, Designation E-96-80 as follows. For the purposes of the present invention, 3 inch diameter (76 mm) circular samples are cut from the test material and from a control material, CELGARD® 2500 (Hoechst Celanese Corporation). CELGARD 2500 is a 0.0025 cm thick film composed of microporous polypropylene. Two or three samples are prepared for each material. Test cups used for testing are cast aluminum, flanged, 5.1 centimeters deep and come with a mechanical seal and neoprene gasket. The cups are distributed by Thwing-Albert Instrument Company, Philadelphia, Pa., under the designation Vapometer cup no. 68-1. One hundred millimeters of distilled water are poured into each Vapometer cup, and each of the individual samples of the test materials and control material are placed across the top area of an individual cup. Screw-on flanges are tightened to form a seal along the edges of the cups leaving the associated test material or control material exposed to the ambient atmosphere over a 62 millimeter diameter circular area (an open, exposed area of about 30 cm$^2$). The cups are then weighed, placed on a tray, and set in a forced air oven set at 100° F. (38° C.). The oven is a constant temperature oven with external air through it to prevent water vapor accumulation inside. A suitable forced air oven is, for example, a Blue M Power-O-Matic 60 oven distributed by Blue M Electric Co. of Blue Island, Ill. After 24 hours, the cups are removed from the oven and weighed. The preliminary, test WVTR value is calculated as follows:

Test WVTR=[(grams weight loss over 24 hours)×7571]÷24

The relative humidity within the oven is not specifically controlled. Under predetermined set conditions of 38° C. and ambient relative humidity, the WVTR for CELGARD 2500 has been defined as 5000 g/m$^2$-24 hours. Accordingly, CELGARD 2500 is run as a control sample with each test and the resulting values are corrected in accord with the variation of the control relative to its known WVTR.

EXAMPLES

Several laminates were prepared using a three-layer A-B-A cast film sold as Huntsman Type 1885, available from Huntsman Packaging Corp., 199 Edison Drive, Washington, Ga. 30763. The film had a core layer containing 42% by weight linear low density polyethylene and 58% by weight calcium carbonate filler. The film had two skin layers containing a mixture of ethylene vinyl acetate (28% vinyl acetate content), and a heterophasic combination of propylene-ethylene copolymers known as Montell KS-037P catalloy. The skin layers constituted about 3% of the total film thickness.

The film was stretched in the machine direction to 3.8–4.0 times its original length, yielding a breathable microporous film having a WVTR in excess of 2000 grams/m$^2$-24 hours. The breathable film had a basis weight of 19 grams/square meter.

In a first set of Examples (using low necked spunbond), the breathable film was adhesively laminated to a reversibly necked spunbond web using 3 grams/square meter of Findley H2525A, an adhesive made by Ato Findley of Milwaukee, Wis., a division of Elf Autochem of France. The adhesive was applied with a meltblown die tip. The reversibly necked spunbond was prepared from a commercial polypropylene spunbond having a basis weight of 0.4 ounces/yd.$^2$, passed over 200° F. heated rolls, and drawn by 6% using 100 ft/min unwind rolls and 106 ft/min re-wind rolls with a 16-foot free span between them. The drawing caused necking of the spunbond web from a 17-inch original width to an 11-inch necked width (a neck-in of 35%). The necked material was then passed over rolls heated to 200° F., to make the reversibly necked spunbond web, as described in U.S. Pat. No. 4,965,122, issued to Morman, the disclosure of which is incorporated by reference.

In a second set of Examples (using high necked spunbond), the same meltblown adhesive was used at the same level, to bond the breathable film and necked spunbond web. The highly necked spunbond was prepared from a commercial polypropylene spunbond having a basis weight of 0.5 ounces per yd.$^2$, which was thermally point bonded at 305° F. The spunbond web was necked prior to entering and in an oven set at 260° F., from a 123-inch original width to a 44-inch necked width (a first neck-in of 64%). The web was slit to a 17-inch width. A roll of the 17-inch wide material was unwound and further necked to a 14-inch width (for a total neck-in of 70%) before being adhesively bonded to the breathable microporous film.

In a third set of Examples (using a spunbond prepared from crimped fibers), the same meltblown adhesive was used at the same level, to bind the breathable film to the spunbond web. The spunbond web was thermally point bonded, and made from side-by-side bicomponent fibers. The bicomponent fibers contained 70% by weight PP3155 polypropylene from Exxon Chemical Co. of Houston, Tex.; extruded adjacent to 30% by weight REXflex® FPO (flexible polyolefin) WL201 from Huntsman Chemical Corp., which is a propylene copolymer. The spunbond web had a basis weight of 0.67 ounces/square yard and a cross-directional peak elongation of 200%.

The data set forth below, for each of the Examples, were generated using the following Procedure For One Cycle/Hold Tensile Test.

Procedure for One Cycle/Hold Tensile Test

A sample of laminate material is cut to 3" long (MD) and 6" wide (CD). An MTS Sintec Model 1/S (Serial #1S/062196/197) is used to evaluate the permanent set properties of the material. The gauge length is 3", and the area of material being tested was 9 square inches (3"×3"). The crosshead speed is set to 1000 mm/min to simulate the extension the material would experience in diaper donning. The material is held at full elongation for 60 seconds. The cycle elongation is set to the various elongations of interest. The elongation is set 3% lower than the actual target because it was found that the Sintec will slightly overshoot the set elongation because of the high crosshead speed. For example, if a 50% elongation and hold is desired, the cycle elongation is set to 47%.

The material is clamped in the jaws. The material is stretched in the sample length (cross direction of the material) to the desired elongation (25%, 50%, 100%, 150%, or 200%) and held in the elongated state for 60 seconds. The jaws are then returned to their original start position.

For the following Examples, two hundred data points were collected and recorded by the computer for each of the three step procedure: 1) elongation, 2) hold and 3) return to zero. The data analyzed was: 1) the force on the sample for the last data point before the crosshead stopped during the elongation step 2) the force on the sample just before the crosshead started to return to zero, 3) the actual elongation of the sample, and 4) the elongation of the sample when the force on the sample returned to 10 grams or less during the "return to zero" step.

Examples 1 and 2

(First Set)

For Example 1, the laminate prepared using the low necked spunbond material described above was extended in the cross direction by 25% of its initial width, then held for 60 seconds, then permitted to retract. For Example 2, the low necked spunbond material was extended in the cross direction by 50% of its initial width, then held for 60 seconds, then permitted to retract. Three samples were run for each Example, and the results were averaged. The following average results were determined.

TABLE 1

| Example No. | % Extension | Force at Extended Width, grams, no delay | Force Drop at Extended Width, 1-min delay | % Permanent Set | % Retraction |
|---|---|---|---|---|---|
| 1 | 25 | 530 | 52% | 74% | 26% |
| 2 | 50 | 768 | 47% | 82% | 18% |

As shown above, the laminate made using the breathable microporous film and the low neck-stretched spunbond can be extended in the cross direction by 25% or 50% of its original width without rupturing. After being held at the stretched width for one minute, the laminate retracts, in both cases, by less than 30% of the difference between the stretched width and the original, unstretched width.

Examples 3–6

(Second Set)

For Example 3, the laminate prepared using the highly necked spunbond material described above was extended in the cross direction by 50% of its initial width, then held for 60 seconds, then permitted to retract. Similar procedures were followed for Examples 4–6, except that the material was extended in the cross direction by 100%, 150%, and 200%, respectively. Again, three samples were run for each Example, and the results were averaged. The following average results were determined.

TABLE 2

| Example No. | % Extension | Force at Extended Width, grams, no delay | Force Drop at Extended Width, 1-min delay | % Permanent Set | % Retraction |
|---|---|---|---|---|---|
| 3 | 50 | 583 | 50% | 74% | 26% |
| 4 | 100 | 650 | 51% | 78% | 22% |
| 5 | 150 | 858 | 51% | 80% | 20% |
| 6 | 200 | 1205 | 48% | 83% | 17% |

As shown above, the laminate made using the breathable microporous film and the highly neck-stretched spunbond web can be extended in the cross direction by 50%, 100%, 150% or 200% without rupturing. After being held at the stretched width for one minute, the laminate retracts, in all cases, by less than 30% of the difference between the stretched width and the original, unstretched width.

Examples 7–10

(Third Set)

For Example 7, the laminate prepared using the spunbond prepared from crimped fibers, as described above, was extended in the cross direction by 50% of its initial width, then held for 60 seconds, then permitted to retract. Similar procedures were followed for Examples 8–10, except that the laminate was extended in the cross direction by 100%, 150% and 200%, respectively. Again, three samples were run for each Example, and the results were averaged. The following average results were determined.

TABLE 3

| Example No. | % Extension | Force at Extended Width, grams, no delay | Force Drop at Extended Width, 1-min delay | % Permanent Set | % Retraction |
|---|---|---|---|---|---|
| 7 | 50 | 505 | 49% | 79% | 21% |
| 8 | 100 | 678 | 47% | 81% | 19% |
| 9 | 150 | 850 | 47% | 82% | 18% |
| 10 | 200 | 1135 | 46% | 82% | 18% |

As shown above, the laminate made using the breathable microporous film and spunbond web prepared from an extendible polymer combination, can be extended in the cross direction by 50%, 100%, 150% or 200% without rupturing. After being held at the stretched width for one minute, the laminate retracts, in all cases, by less than 30% of the difference between the stretched width and the original, unstretched width.

While the embodiments of the invention disclosed herein are presently considered preferred, various modifications and improvements can be made without departing from the spirit and scope of the invention. The scope of the invention is indicated by the appended claims, and all changes that fall within the meaning and range of equivalents are intended to be embraced therein.

We claim:

1. A substantially liquid-impermeable laminate that is conformable to contours of a wearer's body, the laminate comprising:

a film that is extendible in a cross direction to a stretched width at least 25% greater than an original, unstretched width upon application of a stretching force, and retractable by zero to not more than 30% of a difference between the stretched width and the original width upon relaxation of the stretching force after 60 seconds; and laminated to the film, a fibrous nonwoven web that is extendible in a cross direction to a stretched width at least 25% greater than an original, unstretched width upon application of the stretching force, and retractable by not more than 30% of a difference between the stretched width and the original width upon relaxation of the stretching force; and the nonwoven web is extended to cause elongation in a machine direction prior to being laminated to the film;

the film is extended to cause elongation in a machine direction prior to being laminated to the nonwoven web; and the laminate of the extended nonwoven web and the extended film is further extended after lamination to cause elongation in a machine direction and narrowing in its cross direction to form rugae in the film, each ruga extending in the machine direction.

2. The laminate of claim 1, wherein the film and fibrous nonwoven web are extendible in the cross direction to stretched widths at least 35% greater than their original, unstretched widths upon application of a stretching force.

3. The laminate of claim 1, wherein the film and fibrous nonwoven web are extendible in the cross direction to stretched widths at least 50% greater than their original, unstretched widths upon application of a stretching force.

4. The laminate of claim 1, wherein the nonwoven web is neck-stretched to cause elongation in a machine direction and narrowing in its cross direction prior to being laminated to the film.

5. The laminate of claim 1, wherein the nonwoven web comprises fibers made from an extendible polymer.

6. The laminate of claim 1, wherein the nonwoven web comprises crimped fibers.

7. The laminate of claim 1, wherein the film comprises a breathable film.

8. The laminate of claim 6, wherein the film comprises a breathable extendible polymer.

9. The laminate of claim 6, wherein the film comprises a mixture of an inorganic particulate filler and an extendible polymer.

10. The laminate of claim 1, wherein the nonwoven web comprises a spunbond web.

11. The laminate of claim 1, wherein the nonwoven web comprises a meltblown web.

12. The laminate of claim 1, wherein the nonwoven web comprises a bonded carded web.

13. The laminate of claim 1, wherein the nonwoven web comprises an air laid web.

14. The laminate of claim 1, wherein the nonwoven web comprises more than one layer.

15. The laminate of claim 4, wherein the nonwoven web comprises a polymer selected from non-extendible polyolefins, polyamides, polyesters, linear low density polyethylenes having a density of 0.900–0.935 grams/cm$^3$, propylene-alpha olefin copolymers containing at least 90% by weight propylene, and combinations thereof.

16. The laminate of claim 5, wherein the nonwoven web comprises an extendible polymer selected from extendible polyolefins, ethylene-alpha olefin copolymers having a density less than 0.900 grams/cm$^3$, propylene-alpha olefin copolymers containing more than 10% by weight of an alpha-olefin comonomer, heterophasic propylene-ethylene copolymers, propylene polymers containing both atactic and isotactic propylene groups, and combinations thereof.

17. The laminate of claim 1, wherein the film comprises an extendible polymer selected from extendible polyolefins, ethylene-alpha olefin copolymers having a density less than 0.900 grams/cm$^3$, propylene-alpha olefin copolymers containing more than 10% by weight of an alpha-olefin comonomer, heterophasic propylene-ethylene copolymers, propylene polymers containing both atactic and isotactic propylene groups, and combinations thereof.

18. A personal care absorbent article comprising the laminate of claim 1.

19. A medical absorbent article comprising the laminate of claim 1.

20. The laminate of claim 1, wherein the rugae are easily pulled flat in the cross direction.

21. The laminate of claim 1, wherein the film is further extendible in the cross direction after the rugae are pulled flat.

22. The laminate of claim 1, wherein the material of the nonwoven web is extendible or neckable.

23. The laminate of claim 1, wherein the material of the film is a flexible polyolefin.

24. The laminate of claim 1, wherein the amount of extension to the necked web before lamination is about 12.5%.

25. The laminate of claim 1, wherein the amount of extension to the laminate after lamination is about 11.1%.

26. The laminate of claim 1, wherein the amount of extension to the film before lamination is about 350%.

27. The laminate of claim 26, wherein the amount of extension to the film before lamination is about 350%.

28. A substantially liquid-impermeable laminate that is conformable to contours of a wearer's body, the laminate comprising:

a film that is extendible in a cross direction to a stretched width at least 25% greater than an original, unstretched width upon application of a stretching force, and retractable by zero to not more than 30% of a difference between the stretched width and the original width upon relaxation of the stretching force after 60 seconds; and laminated to the film, a fibrous nonwoven web that is extendible in a cross direction to a stretched width at least 25% greater than an original, unstretched width upon application of the stretching force, and retractable by not more than 30% of a difference between the stretched width and the original width upon relaxation of the stretching force; and the nonwoven web is extended to cause elongation in a machine direction prior to being laminated to the film; and the laminate of the extended nonwoven web and the film is further extended after lamination to cause elongation in a machine direction and narrowing in its cross direction to form rugae in the film, each ruga extending in the machine direction.

29. The laminate of claim 28, wherein the rugae are easily pulled flat in the cross direction.

30. The laminate of claim 28, wherein the film is further extendible in the cross direction after the rugae are pulled flat.

31. The laminate of claim 28, wherein the material of the nonwoven web is extendible or neckable.

32. The laminate of claim 28, wherein the material of the film is a flexible polyolefin.

33. The laminate of claim 28, wherein the amount of extension to the necked web before lamination is about 12.5%.

34. The laminate of claim 28, wherein the amount of extension to the necked web after lamination is about 11.1%.

35. A breathable, substantially liquid-impermeable laminate that is extendible in a cross direction to a stretched width at least 25% greater than an original, unstretched width upon application of a stretching force, and retractable by zero to not more than 30% of a difference between the stretched width and the original width upon relaxation of the stretching force after 60 seconds, the laminate comprising:
- a breathable microporous film having cross-directional extendibility at least as great as the laminate; and
- a nonwoven web having cross-directional extendibility at least as great as the laminate; and
- wherein said microporous film cross-directional extendibility comes from flattening rugae formed in the film and from stretching of the film beyond the flattening of the rugae.

36. The laminate of claim 35, wherein the breathable microporous film comprises a mixture of an extendible thermoplastic polymer and an inorganic particulate filler, formed into a film and stretch-thinned in a machine direction.

37. The laminate of claim 35, wherein the stretched width is about 25–75% greater than the original, unstretched width.

38. The laminate of claim 35, wherein the stretched width is about 35–65% greater than the original, unstretched width.

39. The laminate of claim 35, wherein the nonwoven web comprises a neck-stretched material.

40. The laminate of claim 35, wherein the nonwoven web comprises an extendible polymer material.

41. The laminate of claim 35, wherein the nonwoven web comprises crimped fibers.

42. A personal care absorbent article comprising the laminate of claim 35.

43. A medical garment comprising the laminate of claim 35.

44. A breathable, substantially liquid impermeable laminate having a WVTR of at least 300 grams/m$^2$-24 hours, comprising:
- a breathable microporous film extendible in a cross direction to a stretched width at least 25% greater than an original, unstretched width upon application of a stretching force; and
- a thermoplastic fibrous nonwoven web extendible in a cross direction to a stretched width at least 25% greater than an original, unstretched width upon application of the stretching force;
- wherein the film and nonwoven web are aligned with a machine direction of the film substantially parallel to a machine direction of the web; and
- the laminate retracts by 0–30% of a difference between a stretched width and an original, unstretched width when the stretching force is removed after 60 seconds; and
- wherein the film and web are partially stretched before bonding and further stretched after bonding.

45. The laminate of claim 44, wherein the WVTR is at least 1200 grams/m$^2$-24 hours.

46. The laminate of claim 44, wherein the WVTR is at least 2000 grams/m$^2$-24 hours.

47. The laminate of claim 44, wherein the film and web are thermally bonded together.

48. The laminate of claim 44, wherein the film and web are adhesively bonded together.

49. The laminate of claim 44, wherein the film and web are ultrasonically bonded together.

50. A diaper comprising the laminate of claim 44.

51. Training pants comprising the laminate of claim 44.

52. Swim wear comprising the laminate of claim 44.

53. Absorbent underpants comprising the laminate of claim 44.

54. An adult incontinence product comprising the laminate of claim 44.

55. A feminine hygiene product comprising the laminate of claim 44.

56. A medical product comprising the laminate of claim 44.

57. A breathable, substantially liquid impermeable laminate having a WVTR of at least 300 grams/m$^2$-24 hours, comprising:
- a breathable microporous film extendible in a cross direction to a stretched width at least 50% greater than an original, unstretched width upon application of a stretching force; and
- a thermoplastic fibrous nonwoven web extendible in a cross direction to a stretched width at least 50% greater than an original, unstretched width upon application of the stretching force;
- wherein the film and nonwoven web are aligned with a machine direction of the film substantially parallel to a machine direction of the web; and
- the laminate exhibits a drop in retractive force of at least about 35% after being extended to a stretched width 50% greater than the unstretched width, and maintained at the stretched width for 60 seconds; and
- wherein the film and web are partially stretched before bonding and further stretched after bonding.

58. The laminate of claim 57, wherein the drop in retractive force is at least about 45%.

59. The laminate of claim 57, wherein the WVTR is at least 2000 grams/m$^2$-24 hours.

60. The laminate of claim 57, wherein the film and web are thermally bonded together.

61. The laminate of claim 57, wherein the film and web are adhesively bonded together.

62. The laminate of claim 57, wherein the film and web are ultrasonically bonded together.

63. A diaper comprising the laminate of claim 57.

64. Training pants comprising the laminate of claim 57.

65. Swim wear comprising the laminate of claim 57.

66. Absorbent underpants comprising the laminate of claim 57.

67. An adult incontinence product comprising the laminate of claim 57.

68. A feminine hygiene product comprising the laminate of claim 57.

69. A medical product comprising the laminate of claim 57.

* * * * *